(12) United States Patent
Jacobs (10) Patent No.: US 8,480,641 B2
(45) Date of Patent: Jul. 9, 2013

(54) NEGATIVE PRESSURE WOUND TREATMENT APPARATUS AND METHOD

(75) Inventor: Harold L Jacobs, Scarsdale, NY (US)

(73) Assignee: Premco Medical Systems, Inc., New Rochelle, NY (US)

( * ) Notice: Subject to any disclaimer, the term of this patent is extended or adjusted under 35 U.S.C. 154(b) by 18 days.

(21) Appl. No.: 12/997,662

(22) PCT Filed: Jun. 15, 2009

(86) PCT No.: PCT/US2009/003567
§ 371 (c)(1),
(2), (4) Date: Dec. 13, 2010

(87) PCT Pub. No.: WO2009/151645
PCT Pub. Date: Dec. 17, 2009

(65) Prior Publication Data
US 2011/0092958 A1    Apr. 21, 2011

Related U.S. Application Data

(60) Provisional application No. 61/131,925, filed on Jun. 13, 2008.

(51) Int. Cl.
*A61M 1/00* (2006.01)
(52) U.S. Cl.
USPC .................. 604/318; 604/317; 604/319
(58) Field of Classification Search
None
See application file for complete search history.

(56) References Cited

U.S. PATENT DOCUMENTS

| 5,189,919 | A | * | 3/1993 | Hernandez | 73/863.43 |
| 5,967,979 | A | | 10/1999 | Taylor et al. | |
| 6,695,823 | B1 | | 2/2004 | Lina et al. | |
| 6,856,821 | B2 | | 2/2005 | Johnson | |
| 7,648,488 | B2 | | 1/2010 | Smith et al. | |
| 2001/0020146 | A1 | * | 9/2001 | Satterfield et al. | 604/24 |
| 2002/0143286 | A1 | * | 10/2002 | Tumey | 604/11 |
| 2002/0183702 | A1 | | 12/2002 | Henley et al. | |

(Continued)

FOREIGN PATENT DOCUMENTS

| WO | WO2005/025448 A2 | 3/2005 |
| WO | WO 2008040020 A2 * | 4/2008 |

OTHER PUBLICATIONS

International Search Report and Written Opinion issued by the Korean Intellectual Property Office on Jan. 14, 2010 for International Application No. PCT/US2009/003567, (7 pages).
"Effectiveness of a New Antimicrobial Gauze Dressing as a Bacterial Barrier," Reitsma, M.D., Angelique M., et al., University of Virginia Health System, Charlottesville, Virginia, Tyco Healthcare Kendall, H-5273, Sep. 2001.
"Partial Pressure Explained (hopefully) Imperial Units," Micjan, Ron, Dec. 3, 2004; retrieved from Internet address http://www.tmishop.com/math1.htm on Nov. 28, 2007.

*Primary Examiner* — Melanie Hand
*Assistant Examiner* — Joshua Lee
(74) *Attorney, Agent, or Firm* — Faegre Baker Daniels LLP (57) ABSTRACT

A wound treatment apparatus includes a negative pressure source, a bandage configured to cover a wound and provide a sealed region around the wound, a drainage tube coupled to the bandage and the negative pressure source to drain fluid from the wound. The apparatus also includes a controller coupled to the negative pressure source.

23 Claims, 6 Drawing Sheets

U.S. PATENT DOCUMENTS

| | | |
|---|---|---|
| 2003/0078470 A1* | 4/2003 | Borst et al. .................. 600/37 |
| 2005/0065484 A1* | 3/2005 | Watson, Jr. ................. 604/289 |
| 2005/0203452 A1 | 9/2005 | Weston et al. |
| 2005/0222527 A1 | 10/2005 | Miller et al. |
| 2006/0129137 A1 | 6/2006 | Lockwood et al. |
| 2006/0196529 A1* | 9/2006 | Kenowski et al. .......... 134/56 R |
| 2007/0005028 A1* | 1/2007 | Risk et al. .................. 604/315 |
| 2007/0118096 A1* | 5/2007 | Smith et al. ................ 604/541 |
| 2007/0219532 A1* | 9/2007 | Karpowicz et al. ......... 604/540 |
| 2007/0233022 A1 | 10/2007 | Henley et al. |
| 2007/0276195 A1 | 11/2007 | Xu et al. |
| 2007/0276309 A1 | 11/2007 | Xu et al. |

* cited by examiner

NEGATIVE PRESSURE WOUND TREATMENT APPARATUS AND METHOD

CROSS-REFERENCE TO RELATED APPLICATIONS

This application is a nationalization of PCT Patent Application Serial No. PCT/US2009/003567, filed on Jun. 15, 2009, which claims the benefit of U.S. Provisional Application Ser. No. 61/131,925, filed Jun. 13, 2008, the disclosures of which are expressly incorporated herein by reference.

BACKGROUND AND SUMMARY OF THE INVENTION

The present invention relates to a wound treatment apparatus and method. More particularly the present invention relates to a wound treatment apparatus and method using negative pressure therapy to treat a wound.

The use of negative pressure for treating wounds is well known. The apparatus of the present invention provides improvements over conventional negative pressure wound treatment devices.

For illustrative purposes, the wound treatment apparatus and method of the present invention may be used to treat the following exemplary conditions:

1. Acute surface wounds, chronic surface wounds and wounds that reopen after initial closure.
2. Sinus tract, tunnel or fistula located on the surface of the body.
3. Removing edema from wounds/periwound tissue after surgery.
4. Treating skin and deep tissue injury secondary to burns (after patient stabilization and wound debridenient).
5. Positional stabilization of skin flaps and grafts.

In an illustrated embodiment of the present disclosure, a wound treatment apparatus includes a negative pressure source; a bandage configured to cover a wound and provide a sealed region around the wound; a drainage tube coupled to the bandage and the negative pressure source to drain fluid from the wound; and a controller coupled to the negative pressure source. The apparatus also includes at least one of an oxygen sensor, a carbon dioxide sensor, a pH sensor, and a temperature sensor in fluid communication with the drainage tube to provide at least one of an oxygen saturation level of fluid drained from the wound, a carbon dioxide level fluid drained from the wound, a pH level of fluid drained from the wound, and a temperature of fluid drained from the wound, respectively.

In an illustrated embodiment, the at least one sensor is coupled to the controller so that the controller controls the negative pressure source based at least one output signal from the at least one sensor. The controller may be configured to adjust the negative pressure source based the at least one output signal from the at least one sensor to maintain at least one of the oxygen saturation level, the carbon dioxide level, the pH level, and the temperature of the wound at substantially a desired level. In one embodiment, the oxygen sensor, the carbon dioxide sensor, the pH sensor, and the temperature sensor are all simultaneously in fluid communication with the drainage tube, the oxygen sensor, the carbon dioxide sensor, the pH sensor, and the temperature sensor being coupled to the controller so that the controller controls the negative pressure source based output signals from the sensors.

In another illustrated embodiment of the present disclosure, a method of treating a wound includes providing a wound treatment apparatus having a negative pressure source, a bandage configured to cover the wound and provide a sealed region around a perimeter of the wound, at least one drainage tube coupled to the bandage and the negative pressure source, a controller coupled to the negative pressure source, and a data collector coupled to the at least one drainage tube and the controller. The method also includes transmitting data collected by the data collector from the controller of the wound treatment apparatus to a caregiver's computer and/or an insurance company's computer at a remote location via a communication network. In one embodiment, the method includes receiving control instructions with the controller of the wound treatment apparatus from the caregiver's computer at the remote location via the communication network, the control instructions being used by the controller to adjust a therapy applied to the wound by the wound treatment apparatus. In another embodiment, the method includes receiving a reimbursement authorization from the insurance company's computer at the controller of the wound treatment apparatus via the communication network, and beginning a treatment therapy using the controller of the wound treatment apparatus after receipt of the authorization from the insurance company's computer.

Additional features of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The above-mentioned and other features of this invention, and the manner of attaining them, will become more apparent and the invention itself will be better understood by reference to the following description of illustrated embodiments of the invention taken in conjunction with the accompanying drawings, wherein.

DETAILED DESCRIPTION OF THE DRAWINGS

For the purposes of promoting an understanding of the principles of the invention, reference will now be made to certain illustrated embodiments and specific language will be used to describe the same. It will nevertheless be understood that no limitation of the scope of the invention is thereby intended. Alterations and modifications of the invention and such further applications of the principles of the invention as described herein as would normally occur to one skilled in the art to which the invention pertains, are contemplated, and desired to be protected.

Figure 1:
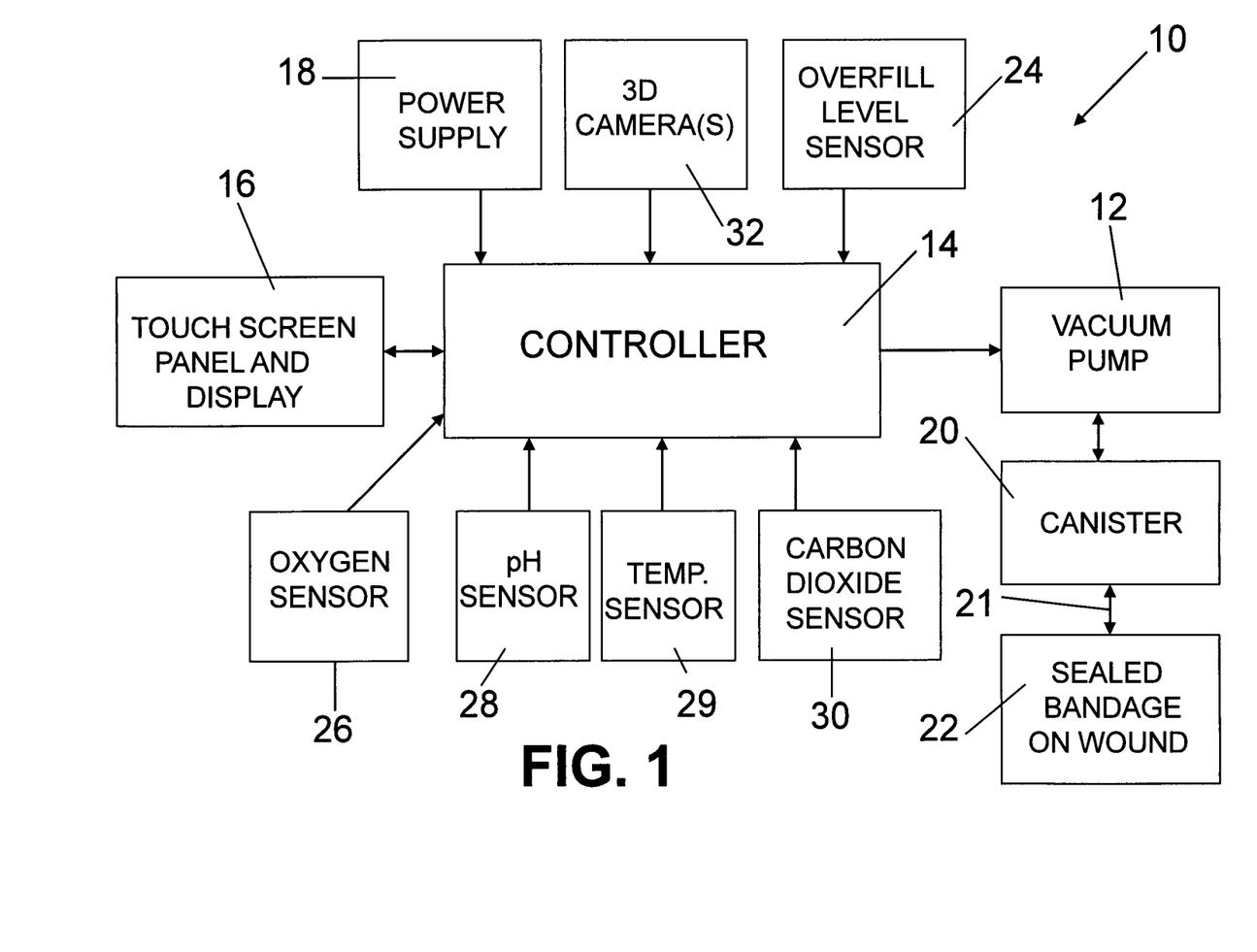
FIG. 1 is a block diagram illustrating components of the wound therapy apparatus of the present invention.

Referring now to the drawings, FIG. 1 is a block diagram of components of a wound treatment apparatus 10 of the present invention. The wound treatment apparatus includes a vacuum pump 12 or other suitable negative pressure source controlled by a controller 14 which illustratively includes a microprocessor. The controller 14 is illustratively coupled to a touch screen panel and display 16. Therefore, the controller 14 may display a plurality of menu options for the user on the touch screen display. The user may enter input commands into the controller using the touch screen panel 16. The touch screen panel 16 and display facilitates operation of the wound treatment apparatus 10.

A power supply 18 supplies power to the controller 14 and vacuum pump 12. The power supply is illustratively a 12V DC power supply supplied either from a wall outlet or a backup battery.

Vacuum pump 12 is coupled to a canister 20 and to a sealed bandage 22 on a wound. In one illustrated embodiment, a Chariker-Jeter® bandage is used to provide a sealed bandage 22 on the wound. Drainage from the wound under the sealed bandage 22 is collected in the canister 20. Bandage 22 illustratively includes antimicrobial gauze surrounded by a transparent adhesive dressing. A suction or drainage tube 21 includes a first end portion located below the transparent adhesive dressing and within the gauze and a second end portion connected to the canister 20. It is understood that multiple bandages 22 may be coupled to the same pump 12, if desired.

In an illustrated embodiment, a housing of vacuum pump includes an integral overfill level sensor 24. Illustratively, the overfill level sensor 24 is a capacitive sensor having an output coupled to controller 14. In the illustrated embodiment, canister 20 is mounted directly to a housing of the vacuum pump 12 adjacent the overfill level sensor 24. Therefore, as fluid fills the canister 20, overfill level sensor 24 detects a full condition and communicates with controller 14 to shut off the vacuum pump 12. An illustrated embodiment of the canister 20 is generally opaque except for sight glasses on opposite sides of the canister 20 to permit a visual inspection of the level of fluid in the canister 20. The canister 20 is easily attached via a "slide-on" connection in which the plurality of mounting pegs fixed to the housing of the vacuum pump 12 engage slots formed in the canister 20 to secure the canister 20 to the pump 12. Other coupling techniques for the canister 20 may also be used.

In an illustrated embodiment, the wound treatment apparatus 10 includes an oxygen sensor 26, a pH sensor 28, a temperature sensor 29, and a carbon dioxide sensor 30 coupled to the controller 14. In the illustrative embodiment, the oxygen sensor 26 and carbon dioxide sensor 30 measure an oxygen saturation level and a carbon dioxide saturation level from the drainage tube 21 coupled to the bandage 22. Sensors 26, 28, 29 and 30 may also be located in the canister 20. In an illustrated embodiment, the pH sensor 28 also measures the pH of fluids drained from the wound through drainage tube 21. Temperature sensor 29 also measures the temperature of drainage fluid. Therefore, readings from oxygen sensor 26, pH sensor 28, temperature sensor 29, and carbon dioxide sensor 30 provide actual sensor readings from the wound cavity. Controller 14 monitors the oxygen, pH, temperature and carbon dioxide levels readings and may adjust or regulate the pump pressure automatically based on these levels to improve treatment of the wound.

In an illustrated embodiment, the caregiver may set desired levels for the oxygen saturation level from oxygen sensor 26, the pH level from pH sensor 28, the temperature from temperature sensor 29, and the carbon dioxide level from carbon dioxide sensor 30. Based on the preset levels and the output signals from the sensors 26, 28, 29, 30, the controller may adjust the negative pressure applied by the vacuum pump 12 to the bandage 22 to maintain the oxygen saturation level, the pH level, the temperature, and/or the carbon dioxide level substantially at the preset levels or within predetermined ranges. Threshold levels for each of the sensors 26, 28, 29, 30 may also be set. Therefore, an alarm may be issued by the controller 14 to alert the caregiver if the oxygen saturation level, pH level, temperature, and/or carbon dioxide level cross the preset threshold levels. In one embodiment, the alarm is transmitted to the caregiver's computer 36 through the communication network 34 as discussed below so that the caregiver is alerted to check operation of the wound treatment apparatus 10. In certain embodiments, the controller may not automatically adjust the pressure as discussed above based on the sensor readings. Instead, the sensor readings are provided to the caregiver either at the wound treatment apparatus 10 location or a remote location, and the caregiver then manually makes adjustments to the settings of the wound treatment apparatus 10 to adjust therapy applied to the wound.

In an illustrated embodiment, a 3-D camera 32 is provided to take images of a wound to help with wound assessment. Camera 32 provides images to controller 14. The 3-D camera 32 illustratively takes pictures of a wound to read a depth, a length, a width and a color of the wound. In the illustrative embodiment, two cameras 32 may be used to generate a 3-D model of the wound including any undermining or tunnels which may be formed beneath the surface of the wound. In certain embodiments, a laptop computer may be coupled to the controller 14 to provide additional processing power to generate the 3-D models. In another embodiment, image data from 3-D cameras 32 may be transmitted to a remote location for processing as discussed below.

Figure 2:
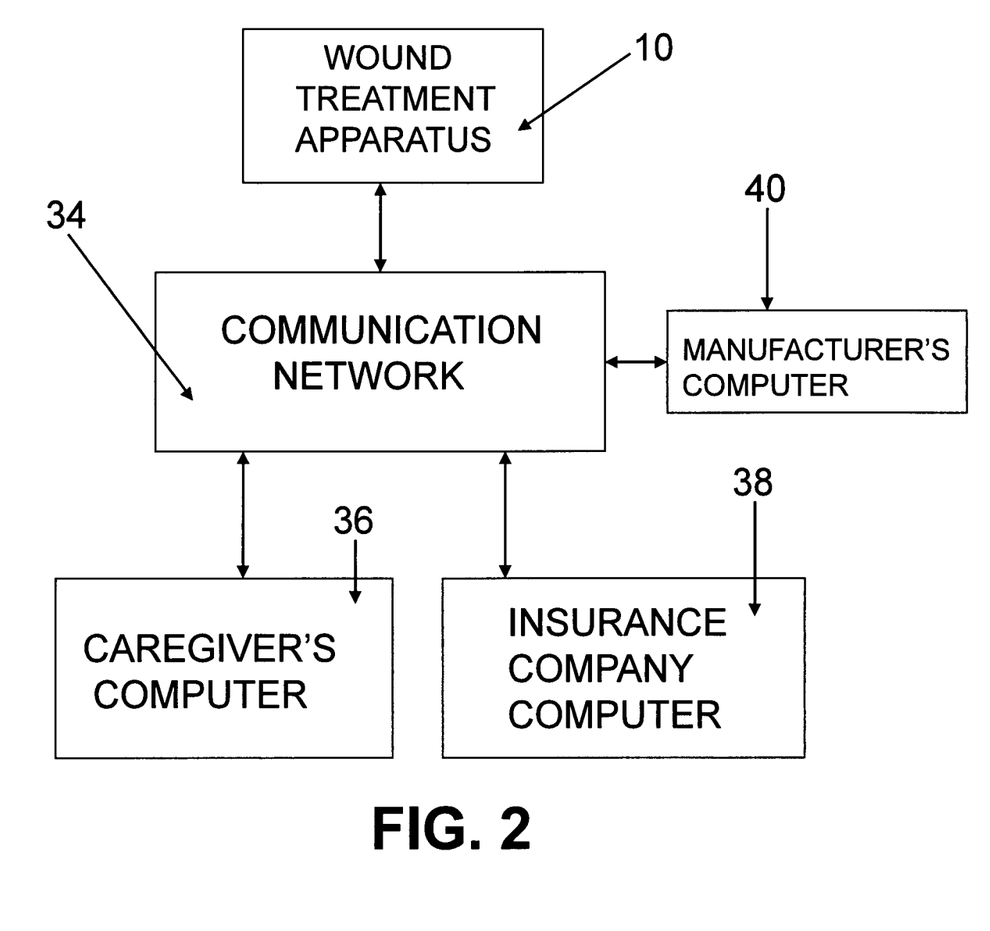
FIG. 2 is a block diagram illustrating communication between the wound therapy apparatus of FIG. 1, a caregiver's computer and an insurance company's computer.

FIG. 2 illustrates the wound treatment apparatus 10 coupled to a communication network 34. Communication network 34 may be any suitable wired or wireless network, such as, for example, cell phone networks, local area networks, wide area networks such as the Internet, or other suitable network for transmitting data from one location to another. Therefore, the controller 14 of wound treatment apparatus 10 can send data and receive data from a caregiver's computer 36 and an insurance company's computer 38 located at remote locations. Illustratively, the controller 14 of wound treatment apparatus 10 may send the data from 3-D camera 32 over communication network 34 to a caregiver's computer 36 or the insurance company's computer 38. The 3-D camera data may be processed to determine the depth, length, width and color of the wound. The insurance company can review the images and make a determination regarding insurance company reimbursement for the therapy based on the images. The controller 14 may receive a reimbursement authorization from the insurance company's computer via the communication network and begin a treatment therapy after receipt of the authorization from the insurance company's computer.

In another embodiment, data such as oxygen saturation level from sensor 26, pH level from sensor 28, temperature from temperature sensor 29, carbon dioxide data from sensor 30, wound images from 3-D camera 32, or other data may be sent to a caregiver's computer 36 at remote a location. The caregiver may then review the data related to the particular wound being treated and adjust the therapy from the remote caregiver's computer 36. In other words, instructions can be sent from caregiver's computer 36 over the communication network 34 to the wound treatment apparatus 10 to adjust the therapy provided to the particular patient. This enables caregivers at a remote location to monitor a plurality of different patients at remote settings or in the patient's home and adjust the therapy applied by wound treatment apparatus 10, if needed.

The end of a particular wound treatment cycle or therapy session also provides a time to change the bandage 22. The wound treatment apparatus 10 stores the elapsed therapy time including any time that the apparatus was shut off during a therapy session in a memory. Wound treatment apparatus 10 also stores the actual pressure applied to the wound during the therapy session and the readings from sensors 26, 28, 29 and 30 during the therapy session. At the end of the therapy session, the data from the therapy session may be automatically sent to the caregiver's computer 36 or the insurance company's computer 38 via an e-mail or other transmission if the wound treatment apparatus 10 is coupled to the communication network 34. Therefore, the caregiver and insurance company can review the therapy session data and make an assessment regarding treatment of the wound. The data also provides an accurate historical database of the therapy sessions. A database may be stored including data for treating wounds, as well as image data from the 3-D camera 32 showing results of the treatment, from a plurality of therapy sessions from a plurality of different patients. By analyzing the database, caregivers and insurance companies may determine the most effective treatment times, pressure levels, or the like for particular types of wounds by analyzing actual results received from a plurality of patients stored in the database. Therefore, new treatment protocols may be developed based on the stored data in the database.

In one embodiment, a size of the wound may be determined using the images obtained by the 3-D camera 32. Controller 14 may calculate a surface area of the wound using the size as determined by the 3-D camera images. Controller 14 may then adjust the negative pressure applied by the vacuum pump 12 based on the size of the wound. For example, as a wound heals and becomes smaller, the initial pressure setting may actually apply a greater pressure to the wound than desired causing discomfort to the patient. Therefore, the controller 14 may automatically reduce the pressure applied by the vacuum pump 12 as the wound size decreases to maintain the effective pressure applied to the wound surface area substantially constant as the wound gets smaller. If the wound gets bigger or otherwise changes, the controller 14 may automatically increase the pressure applied by the vacuum pump 12 to maintain the effective pressure applied to the wound surface area substantially constant as the surface area of the wound gets larger.

Figure 3:
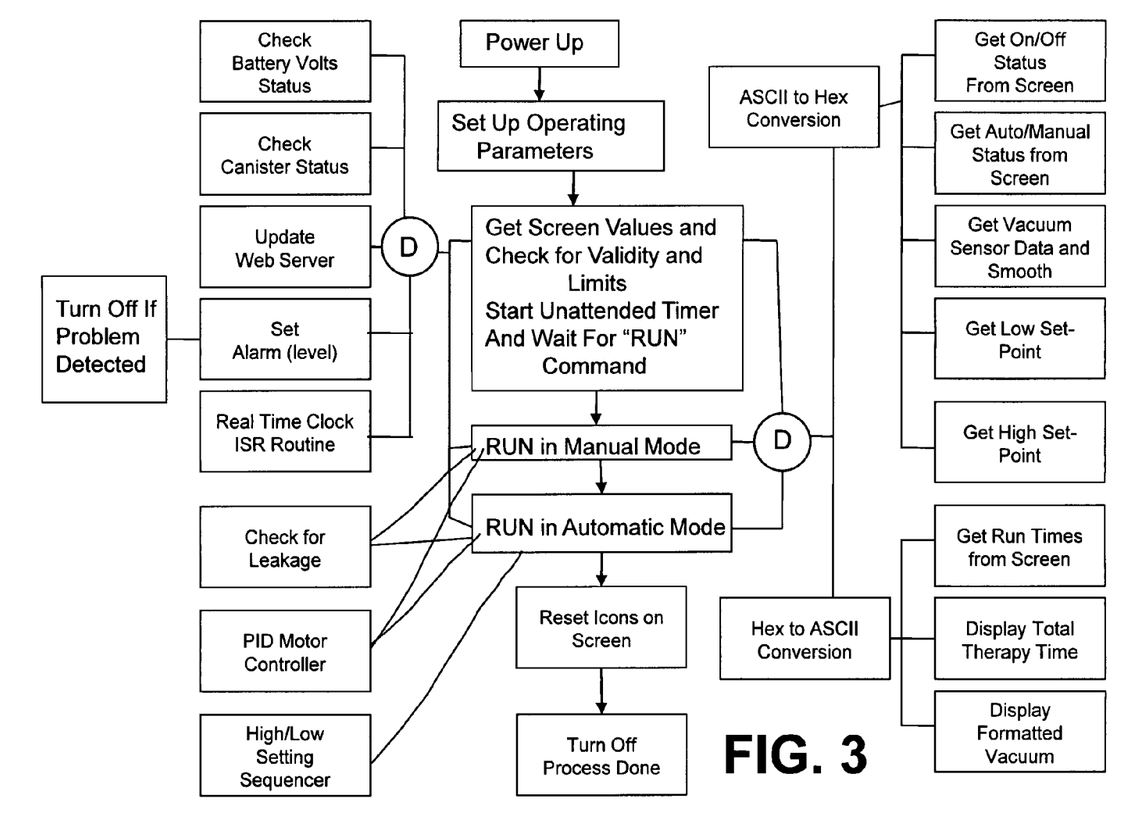
FIG. 3 is a block diagram illustrating operation of the wound treatment apparatus of the present invention.

FIG. 3 illustrates a software flow chart for control of the wound treatment apparatus of the present invention.

Controller 14 monitors operation of the vacuum pump 12 and the drainage tube 21 from the bandage 22 to determine if a leak has occurred in the drainage tube 21 or the bandage 22. If a leak is detected, a visual and/or audio alarm is activated The wound treatment apparatus 10 of the present invention is illustratively controlled by a microprocessor of controller 14 with fully operational touch screen interface. The apparatus 10 adapts easily for use in a general hospital, clinic, outpatient or homecare environment. One illustrated embodiment includes a piston vacuum pump 12 utilizing a microprocessor controller 14 with a custom vacuum feedback device. The vacuum pump motor is illustratively controlled via a proportional duty cycle DC drive. The motor speed is mathematically calculated based on current vacuum pressure (mmHg) and the rate of change of the vacuum until the desired vacuum set point is achieved. This algorithm of the present invention allows the desired negative pressure set point to be maintained within a very close tolerance (such as, for example, +/−2 mmHg pressure variance) without the need for mechanical regulators. It also allows the pump 12 to implement an auto clamp feature on the vacuum so that the vacuum value does not exceed 200 mmHg. This auto clamp feature reduces the likelihood that the patient will receive unwanted sudden alterations in vacuum pressures, and is based on the desired vacuum pressure set point, not a mechanical safety with only one setting.

In an illustrative embodiment, a pressure sensor monitors pressure within the canister 20 at a very fast sampling rate so that the negative pressure level applied to the wound by the vacuum pump 12 is generally continuously monitored by the controller 14. If the actual negative pressure level measured by the pressure sensor within the canister varies from the desired preset level, controller 14 adjusts the vacuum pump 12 to change the negative pressure accordingly in order to maintain the very close tolerance to the actual preset pressure as discussed above. In one illustrated embodiment, the tolerance is maintained at about a +/−2 mmHg pressure variance as discussed above. In another illustrated embodiment, the tolerance is maintained at about a +/−1 mmHg pressure variance. In yet another illustrated embodiment, the tolerance is maintained at about a +/−½ mmHg pressure variance. Such real time feedback control of the pressure within the canister 20 reduces pulsation applied by the vacuum pump 12 to the wound which may occur in conventional wound treatment devices.

The apparatus 10 of the present invention is easy to operate due to the fully operational touch screen 16. Important operational information, such as negative pressure therapy set point, alarms due to canister full, blocked filter, and low battery are in an easy to understand format. The therapy terminates automatically when certain alarm is triggered to protect the unit. Items like Run and Stop switches are configured as easy to use touch cells, not mechanical switches with contacts that are prone to failure. While other vacuum pumps must run at full speed continuously to maintain their negative pressure set point, the pump 12 of the present apparatus 10 runs at the minimum speed required to maintain the vacuum level setting. This makes these units environmentally friendly by reducing the amount of energy needed to provide therapy. Equally important is that the units are lighter and more portable since less energy needs allows for a smaller, lighter battery and thus smaller, lighter device. The battery of the apparatus may illustratively be charged in about 15 minutes and can maintain its charge for about 6 to 8 hours.

Figure 4:
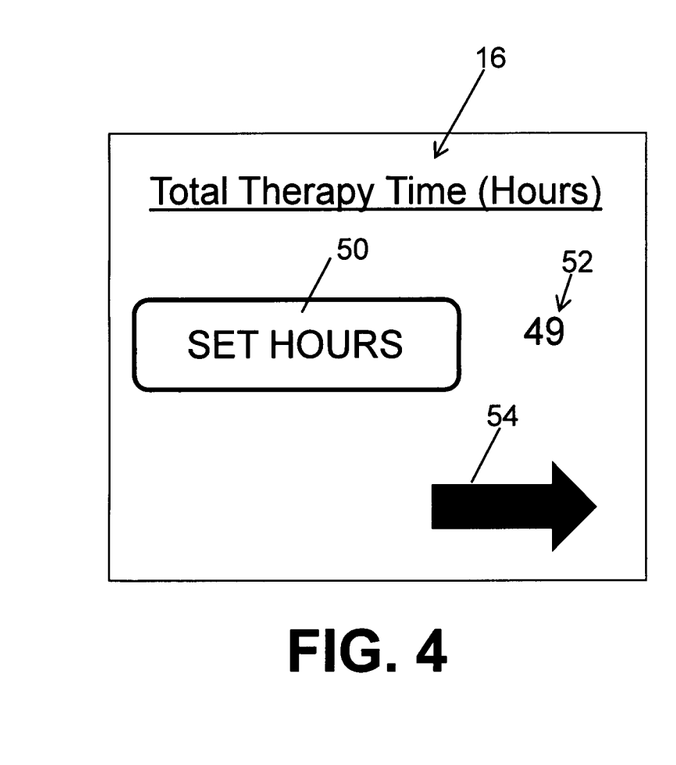
FIGS. 4-8 are illustrative screen displays on a touch screen control panel of the wound treatment apparatus.

FIGS. 4-8 illustrate screen displays on touch screen panel 16 which permit a user to control operation of the wound treatment apparatus 10. The apparatus 10 may be password protected. After entering a password and patient's identification number using a keyboard screen (not shown) on the touch screen panel, the user enters the total therapy time for the wound treatment apparatus as illustrated in FIG. 4. The total therapy time is the total number of hours for one treatment. A user presses the SET HOURS button 50 shown in FIG. 4 to enter the number of hours for treatment. Illustratively, a numerical keypad screen (not shown) will be displayed on touch screen 16 when the SET HOURS button 50 is pressed. User uses the keypad to enter the total therapy time. Illustratively, the total therapy time is between 1 and 255 hours, although any number of hours may be used. The total therapy time entered by the user is illustratively displayed at location 52 on screen 16. When the total elapsed therapy time reaches the entered total therapy time, the apparatus 10 automatically stops the therapy. In an illustrated embodiment, the apparatus will automatically set the total therapy time to 255 hours as a default if the total therapy time is zero. The user can press the arrow 54 to advance to the next screen.

Figure 5:
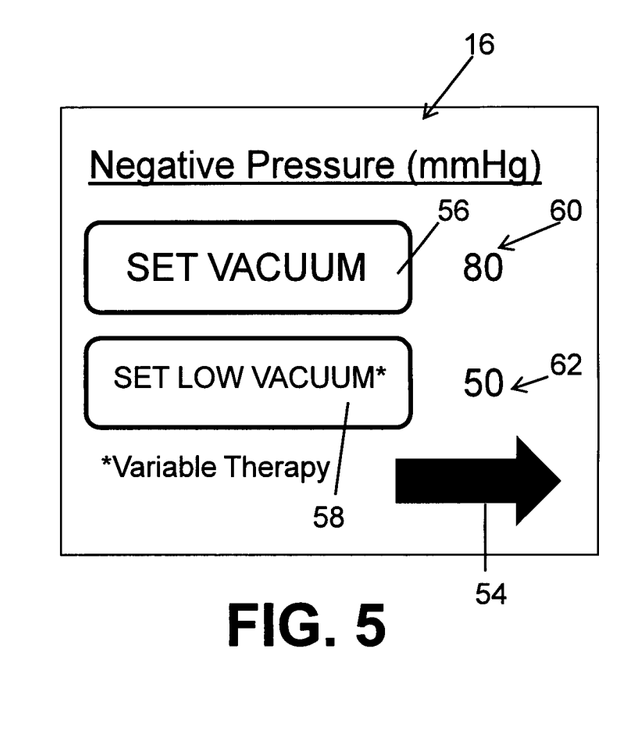

Next, a user inputs the desired negative pressure setting using the screen 16 shown in FIG. 5. The user may press the SET VACUUM button 56 to enter a set point for the negative pressure. If the wound treatment apparatus 10 provides variable therapy, the SET VACUUM button 56 sets the high negative pressure value. The SET LOW VACUUM button 58 is then pressed to input the low vacuum level for variable therapy using the keypad screen as discussed above. Illustratively, the vacuum set point may be set between 20 mmHg and 185 mmHg. Once the user saves the vacuum set points, the set points are displayed at locations 60 and 62 shown in FIG. 5.

Figure 6:
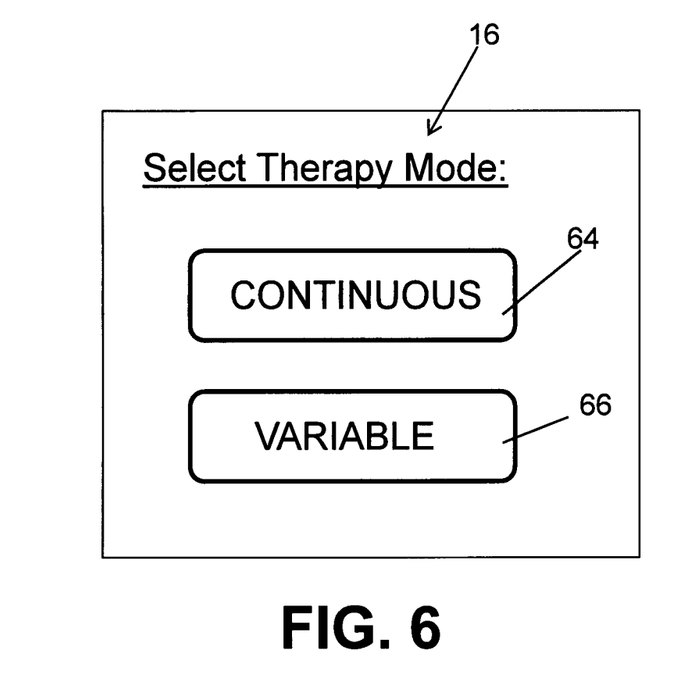
Figure 7:
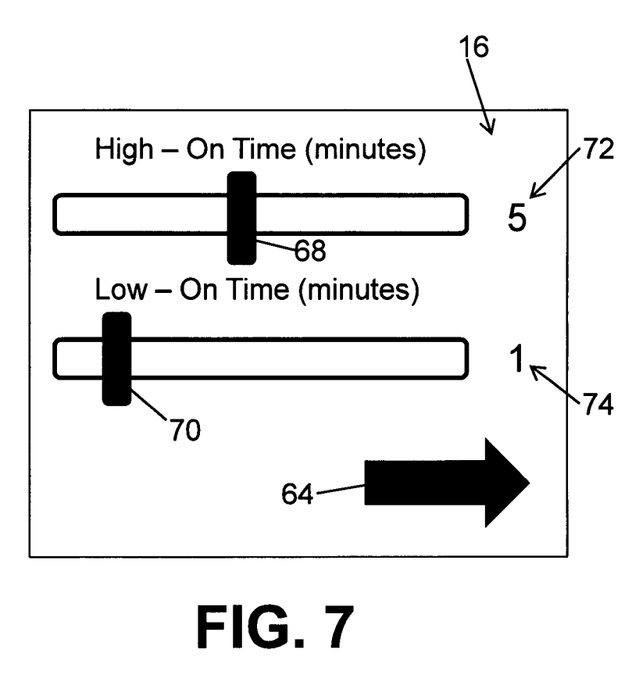

FIG. 6 illustrates the touch screen 16 for selecting between a continuous therapy mode and a variable therapy mode. Illustratively, user presses button 64 for the continuous therapy mode and button 66 for the variable therapy mode. If button 66 is pressed, screen 16 shown in FIG. 7 appears on the touch screen display. The user then uses sliders 68 and 70 to adjust the time for the high negative pressure settings and the low negative pressure settings. Other suitable means such as the keypad screen may also be used for data entry. Illustratively, the high and low settings are between one and ten minutes. The selected values for the high and low intervals are displayed at locations 72 and 74, respectively, in FIG. 7.

Figure 8:
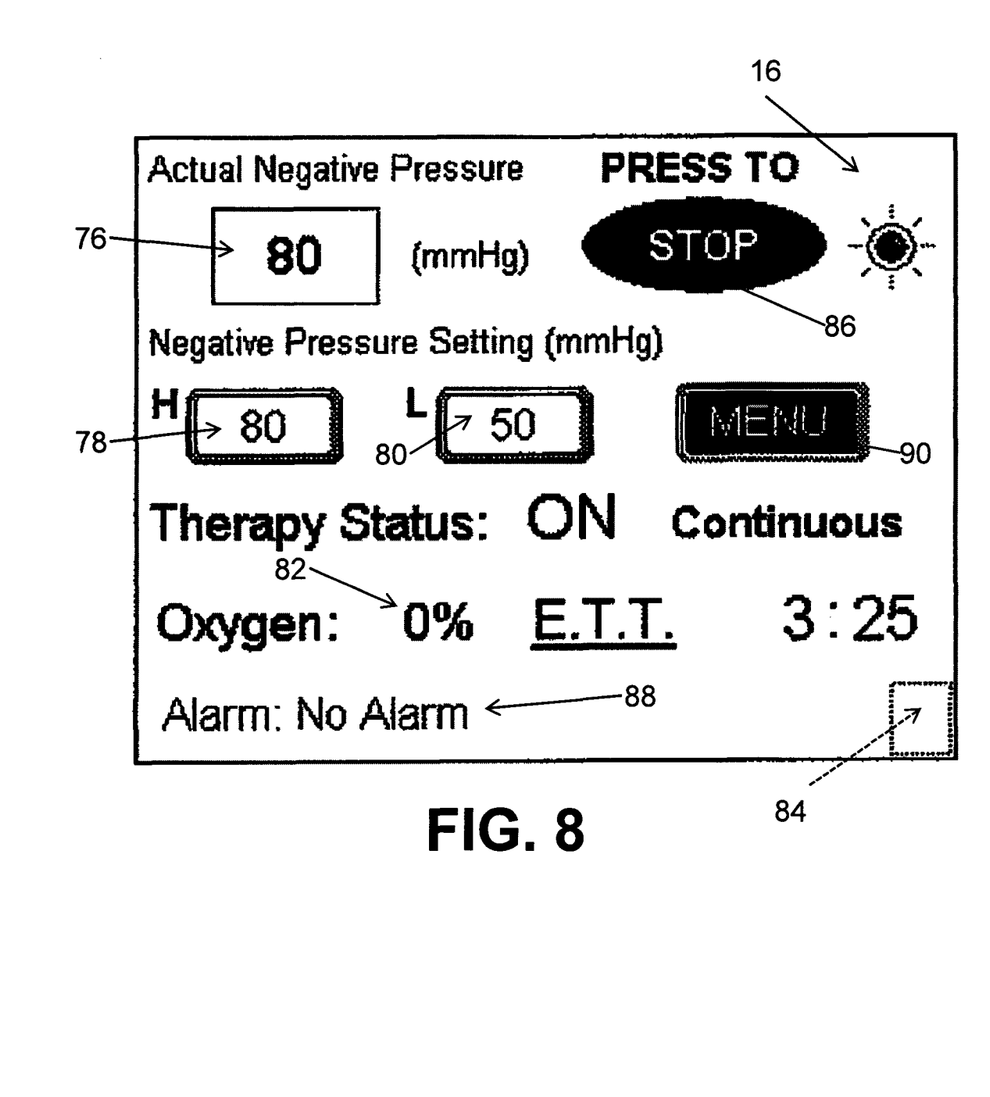

An illustrative operation screen for the wound treatment apparatus 10 is shown in FIG. 8. The actual negative pressure is displayed at location 76. The high and low settings are displayed at locations 78 and 80, respectively. An oxygen percentage is displayed at section 82. In order to reduce the likelihood that a patient may change the settings, there is a hidden button illustratively located in the right bottom corner and shown by dotted lines 84. Pressing the hidden button 84 will make all the controller buttons disappear. Pressing hidden button 84 again will make the controls reappear. When the system is running, a STOP button 86 is displayed. When the system is stopped, a RUN button is displayed at location 86. The apparatus 10 illustratively displays the current therapy status (either on or off) and whether or not the apparatus 10 is in continuous or variable mode. The apparatus 10 also displays the Elapsed Therapy Time (ETT) on display screen 16. The controller 14 keeps track of elapsed therapy time during normal operation of the pump 12. If the patent stops the therapy, the timer stops. In other words, if therapy is stopped by pressing the STOP button 86, the elapsed therapy time is paused until the user presses the RUN button to continue the therapy. Therefore, the caregiver can determine whether or not the patient followed the prescribed treatment regimen since the caregiver's last visit based on the timer. Illustratively, a message such as "Therapy is completed" is displayed on screen 16 when the elapsed therapy time reaches the entered total therapy time. The user may press the menu button 90 to stop therapy and return to the patent identification screen or other location.

If any alarm is triggered, the related alarm message is displayed at location 88. In an illustrated embodiment, the alarm message is provided on the screen under the following conditions:

| ALARM TYPE | NOTIFICATION | REMEDY |
| --- | --- | --- |
| High Vacuum | Visual message "High Vacuum" with audible alarm when the actual negative pressure is 15 mmHg higher than the set point. Device will automatically stop pumping when the set point is reached. Device resumes pumping automatically when the vacuum goes back within the proper set point range. | Push stop button and restart. If alarm persists, discontinue use and contact manufacturer. |
| Canister Full | Visual message "Canister Full" with audible alarm when canister is full; NPWT stops automatically. | Change canister and restart NPWT. |
| Blocked Filter | Visual message "Blocked Filter" with audible alarm when filter is blocked; NPWT stops automatically. | Replace the filter and restart NPWT. |
| Air Leak | Visual message "Air Leak" with audible alarm after leakage is detected. | Check dressing, canister, filter and tubing for leaks. |
| Low Battery | Visual message "Low Battery" and audible alarm (beeps once per minute when low battery detected). | Connect device to AC power source and turn on device to recharge the battery. |
| No Activity | Visual message "No Activity - Turn Therapy On" with audible alarm after 15 minutes without NPWT. (Only occurs when device turned ON for the first time) | Turn therapy ON. |

Illustrative Features of the Wound Treatment Apparatus Include:
  Pressure Controls: Solid state
  Pressure Setting: Adjustable
  Pressure Monitoring: Display actual negative pressure
  Filter: External back up filter with silicon tubing
  Oxygen Sensor: Monitoring the oxygen saturation of the wound as the treatment parameters are changed (such as changing the intensity of the negative pressure, changing the wound contact layer, etc.) improves the wound's response to treatment.
  Carbon Dioxide Sensor: Monitoring a carbon dioxide saturation of the wound as the treatment parameters are changed (such as changing the intensity of the negative pressure, changing the wound contact layer, etc.) improves the wound's response to treatment.
  pH: Monitoring the pH level of sludge coming out of the wound cavity.
  Alarms: Visual and audio alarms (High Vacuum, Blocked Filter, Air Leak, Canister Full, No Activity and Low Battery)
  Therapy Mode Continuous or Variable
  Battery Backup: Up to 6 hours
  Safety features: electronic and manual
  Overflow sensor: A capacitive sensor that monitors the fluid level in the suction canister. If the fluid level reaches the maximum, the unit will stop automatically to prevent the back-up fluid into the pump and patient.
  Overflow valve: A manual safety feature positioned in the cap of the canister. If fluid reaches the maximum level in the canister, the filter or float in the overflow valve will block the inlet port, which will stop the suction automatically. The "Blocked Filter" alarm is then activated and the unit is stopped.
  Accessories:
  Illustrative accessories which may accompany the apparatus of the present invention include:
    A Fluid Collection Bottle/Canister: Lg. 800 ml, Med. 500 ml, Sm. 250 ml
    Filter
    Connection Tube with Adaptor Connector
    10 mm Flat Wound Drain Transparent Adhesive Dressing (Large, Medium and Small)
Antimicrobial Gauze (Large, Medium and Small)
Tubing Clamps (Large and Small)
Tubing Caps Wound Drainage Kit Instructions A medical team and doctor should make an individual assessment of how to apply the wound drainage kit.
These general instructions should be followed:
1. Irrigate the wound thoroughly with normal saline using a syringe.
2. Wipe off any excess saline that might have spilled onto the outer skin; for dressing prep.
3. Measure wound for depth, tunneling and undermining, use the clock method, when assessment of wound is be made.
4. Measure deepest area of wound, shorten length of 10 mm silicone drain tube (21) accordingly, 1 cm less than deepest area in wound bed, tunneling or undermining.
5. Apply antimicrobial sponge to entire wound bed, cover tip of 10 mm silicone drain with antimicrobial gauze, place drain in wound bed. The drain should not be placed in the fistula tract.
6. Select proper size dressing, allow at least one inch of intact skin beyond wound edges. Place dressing over packed wound, crimp dressing around tubing and seal.
7. Set Negative Pressure Wound Therapy Unit, (NPWT) to recommended settings; (approximately 60-80 mmHg), at continuous suction, observe the wound site. The dressing should contract immediately.
8. Check for leaks; listen for sounds, sounds indicate a leak in the dressing. Pat down lightly with your hand around the area where there is sound, until the sound is gone. Again observe the wound dressing, it should be completely contracted.

If the wound is irregular and there is a chance of leakage, check for dressing integrity, each shift change by occluding suction tubing. If dressing balloons, than contracts after releasing the tubing, check dressing for leaks.

In an illustrated embodiment, the wound treatment apparatus may include a security system. Each apparatus 10 is illustratively assigned a serial number. Before operation, the user or caregiver must access a manufacturer's computer 40 (such as via a web site) and enter the serial number to activate the apparatus 10. Manufacturer's computer 40 illustratively sends an access or activation code to the apparatus 10 which must be entered via the touch screen 14 or other input device to begin operation. This permits the manufacturer to monitor operation of the apparatus for billing, servicing or other purposes from a remote location.

U.S. Provisional Patent Application 60/131,925 and Exhibit A thereto, filed on Jun. 13, 2008, are expressly incorporated by reference herein.

While the invention has been illustrated and described in detail in the drawings and foregoing description, the description is to be considered as illustrative and not restrictive in character. Variations and modifications exist within the scope and spirit of the present invention as described and defined in the following claims.

What is claimed is:

1. A method of treating a wound comprising:
providing a wound treatment apparatus having a negative pressure source, a bandage configured to cover the wound and provide a sealed region around a perimeter of the wound, at least one drainage tube coupled to the bandage and the negative pressure source, a controller coupled to the negative pressure source, and a data collector coupled to the at least one drainage tube and the controller;

transmitting data collected by the data collector from the controller of the wound treatment apparatus to at least one of a caregiver's computer and an insurance company's computer at a remote location via a communication network;

receiving a reimbursement authorization from the insurance company's computer at the controller of the wound treatment apparatus via the communication network based on data transmitted from the controller of the wound treatment apparatus to an insurance company's computer at a remote location via the communication network; and beginning a treatment therapy using the controller of the wound treatment apparatus after receipt of the authorization from the insurance company's computer.

2. The method of claim 1, wherein the treatment therapy includes storing actual pressures applied to the wound and an elapsed therapy time during a therapy session in a database to provide a historical database for the therapy session.

3. The method of claim 2, further comprising analyzing the historical database to develop a new treatment protocol.

4. The method of claim 1, wherein the wound treatment apparatus further includes at least one of an oxygen sensor, a carbon dioxide sensor, a pH sensor, and a temperature sensor in fluid communication with the drainage tube to provide at least one of an oxygen saturation level of fluid drained from the wound, a carbon dioxide level fluid drained from the wound, a pH level of fluid drained from the wound, and a temperature of fluid drained from the wound, respectively.

5. The method of claim 4, further comprising adjusting the negative pressure source with the controller based the at least one output signal from the at least one sensor to maintain at least one of the oxygen saturation level, the carbon dioxide level, the pH level, and the temperature of the wound at substantially a desired level.

6. The method of claim 4, further comprising issuing an alarm when at least one of the oxygen saturation level, the carbon dioxide level, the pH level, and the temperature of the wound crosses a preset threshold level.

7. The method of claim 4, wherein at least two of the oxygen sensor, the carbon dioxide sensor, the pH sensor, and the temperature sensor are in fluid communication with the drainage tube and coupled to the controller, and further comprising adjusting the negative pressure source with the controller based on output signals from the at least two sensors.

8. The method of claim 4, wherein at least three of the oxygen sensor, the carbon dioxide sensor, the pH sensor, and the temperature sensor are in fluid communication with the drainage tube and coupled to the controller, and further comprising adjusting the negative pressure source with the controller based on output signals from the at least three sensors.

9. The method of claim 4, wherein the treatment therapy includes sending data from the at least one sensor via a communication network to a caregiver's computer at a remote location, receiving control instructions from the caregiver's computer via the communication network, and adjusting the negative pressure source with the controller based on the received instructions.

10. The method of claim 1, wherein the treatment therapy includes maintaining a negative pressure applied by the negative pressure source at a predetermined set point within a tolerance of 2 mmHg or less.

11. The method of claim 1, wherein the treatment therapy includes maintaining a negative pressure applied by the negative pressure source at a predetermined set point within a tolerance of 1 mmHg or less.

12. A method of treating a wound comprising:
  providing a wound treatment apparatus having a negative pressure source, a bandage configured to cover the wound and provide a sealed region around a perimeter of the wound, at least one drainage tube coupled to the bandage and the negative pressure source, a controller coupled to the negative pressure source, and a data collector coupled to the at least one drainage tube and the controller;
  transmitting identification data from the controller of the wound treatment apparatus to a manufacturer's computer at a remote location via the communication network;
  receiving an activation code from the manufacturer's computer at the controller;
  beginning a treatment therapy using the controller of the wound treatment apparatus after receipt of the activation code from the manufacturer's computer; and
  transmitting data collected by the data collector from the controller of the wound treatment apparatus to at least one of a caregiver's computer and an insurance company's computer at a remote location via a communication network.

13. The method of claim 12, wherein the identification data includes a serial number of the wound treatment apparatus.

14. The method of claim 12, wherein the treatment therapy includes storing actual pressures applied to the wound and an elapsed therapy time during a therapy session in a database to provide a historical database for the therapy session.

15. The method of claim 12, further comprising analyzing the historical database to develop a new treatment protocol.

16. The method of claim 12, wherein the wound treatment apparatus further includes at least one of an oxygen sensor, a carbon dioxide sensor, a pH sensor, and a temperature sensor in fluid communication with the drainage tube to provide at least one of an oxygen saturation level of fluid drained from the wound, a carbon dioxide level fluid drained from the wound, a pH level of fluid drained from the wound, and a temperature of fluid drained from the wound, respectively.

17. The method of claim 16, further comprising adjusting the negative pressure source with the controller based the at least one output signal from the at least one sensor to maintain at least one of the oxygen saturation level, the carbon dioxide level, the pH level, and the temperature of the wound at substantially a desired level.

18. The method of claim 16, further comprising issuing an alarm when at least one of the oxygen saturation level, the carbon dioxide level, the pH level, and the temperature of the wound crosses a preset threshold level.

19. The method of claim 16, wherein at least two of the oxygen sensor, the carbon dioxide sensor, the pH sensor, and the temperature sensor are in fluid communication with the drainage tube and coupled to the controller, and further comprising adjusting the negative pressure source with the controller based on output signals from the at least two sensors.

20. The method of claim 16, wherein at least three of the oxygen sensor, the carbon dioxide sensor, the pH sensor, and the temperature sensor are in fluid communication with the drainage tube and coupled to the controller, and further comprising adjusting the negative pressure source with the controller based on output signals from the at least three sensors.

21. The method of claim 16, wherein the treatment therapy includes sending data from the at least one sensor via a communication network to a caregiver's computer at a remote location, receiving control instructions from the caregiver's computer via the communication network, and adjusting the negative pressure source with the controller based on the received instructions.

22. The method of claim 12, wherein the treatment therapy includes maintaining a negative pressure applied by the negative pressure source at a predetermined set point within a tolerance of 2 mmHg or less.

23. The method of claim 12, wherein the treatment therapy includes maintaining a negative pressure applied by the negative pressure source at a predetermined set point within a tolerance of 1 mmHg or less.

* * * * *

UNITED STATES PATENT AND TRADEMARK OFFICE
CERTIFICATE OF CORRECTION

PATENT NO. : 8,480,641 B2  
APPLICATION NO. : 12/997662  
DATED : July 9, 2013  
INVENTOR(S) : Harold L. Jacobs It is certified that error appears in the above-identified patent and that said Letters Patent is hereby corrected as shown below:

In the Claims:

In Claim 15, column 11, line 30, delete "12" and replace therewith "14"

Signed and Sealed this  
Twenty-fourth Day of September, 2013

Teresa Stanek Rea  
*Deputy Director of the United States Patent and Trademark Office*